United States Patent [19]

Gemmill, Jr. et al.

[11] 4,253,978

[45] Mar. 3, 1981

[54] PHOSPHORUS-CONTAINING COMPOUNDS AND LUBRICANTS CONTAINING SAME

[75] Inventors: Robert M. Gemmill, Jr., Pitman; Andrew G. Horodysky, Cherry Hill, both of N.J.

[73] Assignee: Mobil Oil Corporation, New York, N.Y.

[21] Appl. No.: 80,633

[22] Filed: Oct. 1, 1979

[51] Int. Cl.$^3$ .............................................. C10M 1/48
[52] U.S. Cl. ............................ 252/32.7 E; 252/46.7; 252/51.5 A; 252/51.5 R; 548/113; 548/216; 548/239; 252/49.7
[58] Field of Search ............ 252/32.7 E, 46.7, 51.5 A, 252/51.5 R, 49.7; 548/113, 216, 239

[56] References Cited

U.S. PATENT DOCUMENTS

| | | | |
|---|---|---|---|
| 2,652,367 | 9/1953 | Adelson | 252/46.7 |
| 3,850,822 | 11/1974 | Sleere et al. | 252/46.7 |
| 4,086,173 | 4/1978 | Nnadi et al. | 252/51.5 A |
| 4,193,883 | 3/1980 | Frangatos | 252/51.5 A |

*Primary Examiner*—Jacqueline V. Howard
*Attorney, Agent, or Firm*—Charles A. Huggett; Michael G. Gilman; Claude E. Setliff

[57] ABSTRACT

Metal salts of hydrocarbyl oxazoline phosphorodithioic acids are novel compounds effective for reducing friction and wear when added to a lubricant.

18 Claims, No Drawings

PHOSPHORUS-CONTAINING COMPOUNDS AND LUBRICANTS CONTAINING SAME

BACKGROUND OF THE INVENTION

1. Field of the Invention

The invention is concerned with a novel group of compounds and their use as friction reducing and antiwear additives in lubricants, i.e. lubricant compositions containing same.

2. Dicussion of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine and power transmission systems, because loss of a substantial amount of the theoretical mileage possible from a gallon of fuel is traceable directly to friction.

With respect to the novel compounds of this invention, they are made by (1) forming an oxazoline from one mole of monocarboxylic acid and one mole of a hydroxyamine (e.g. 2-amino-2-(hydroxymethyl)-1,3-propanediol), also known as tris(hydroxymethyl)aminomethane, (2) reacting this with phosphorus sulfide and (3) forming the metal derivative. The reaction to prepare the oxazoline is known and the reaction of the two hydroxyls of the oxazoline with $P_2S_5$ and the formation of the metal derivative are well known. However, no art is known that teaches or suggests the novel compounds or their use as multifunctional friction reducing lubricant additives.

SUMMARY OF THE INVENTION

In accordance with the invention, there is provided a reaction product obtained by reacting one equivalent of a carboxylic acid of the formula

R—COOH wherein R is a hydrocarbyl containing from 9 to 50 carbon atoms with tris(hydroxymethyl)aminomethane, reacting the resulting product with a phosphorus polysulfide, particularly phosphorus pentasulfide, and reacting this product with a metal-containing compound. "Hydrocarbyl" is preferably alkyl, including nonyl, decyl, dodecyl, tetradecyl, octadecyl, eicosyl, and the like, or alkenyl. It can also be aryl, in which the aryl nucleus has 6 to 14 carbon atoms.

The invention also provides a lubricant composition comprising a lubricant and a friction reducing or antiwear amount of the product. It is further contemplated that the product will aid in the reduction of fuel consumption in an internal combustion engine.

DESCRIPTION OF SPECIFIC EMBODIMENTS

As has been mentioned hereinabove, the compounds of this invention can be made by reacting a monocarboxylic acid with a hydroxyamine, reacting the product thus formed with a phosphorus sulfide and then with a metal-containing compound. The following reactions illustrate what we believe to be the major product from the reaction.

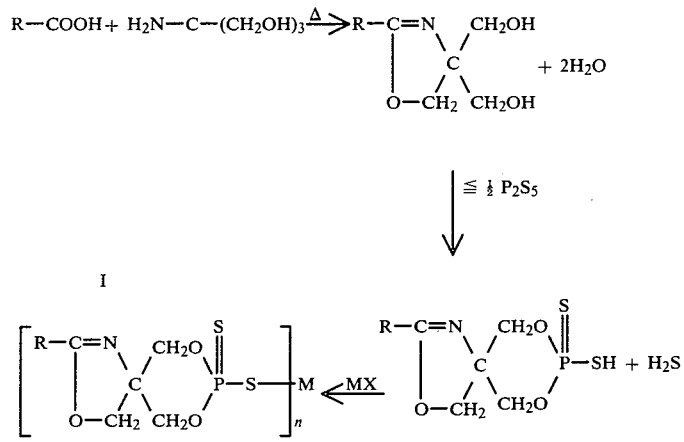

where R is as defined above, M is metal or a metal containing ion and n is equal to the valence of M. However, the reaction with $P_2S_5$ probably produces a complex mixture of products having structures like the following:

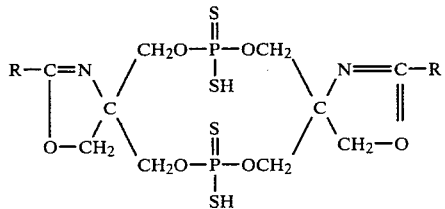

When this and other possible compounds are reacted with metal-containing compound, the mixture becomes even more complex with respect to their presence therein. Since the product is a complex mixture, it will be claimed as a reaction product, although it is believed to contain a predominant amount of compound I.

The carboxylic acid, as indicated, may have from 9 to 50 carbon atoms, including the carboxyl carbon atom. These include the saturated decanoic (capric), dodecanoic (lauric), tetradecanoic (myristic), octadecanoic (stearyl), eicosanoic (arachidic) acids and the like, as well as the unsaturated acids, including particularly oleic acid.

The first reaction, i.e. between the monocarboxylic acid and the amine, can be carried out at from about 80° C. to about 250° C., preferably from about 120° C. to about 190° C. The temperature chosen will depend for the most part on the reactants chosen and whether or not a solvent is used. In carrying out this reaction, it is essential that quantities of reactants be chosen such that at least two hydroxyls remain for the reaction with the phosphorus sulfide. For example, in the reaction illustrated, one mole of the acid and one mole of the amine are required. An excess of acid in this case would lead to the formation of some monoester oxazoline.

In carrying out the reaction to form the phosphorodithioic acid, stoichiometric amounts of the oxazoline and $P_2S_5$ may be used. Generally, however, a slight excess of $P_2S_5$, not exceeding about 2 to 10% by weight is preferred. The final reaction, i.e. with the metal compound, can be carried out at from about 50° C. to about 125° C., preferably from about 70° C. to about 100° C. Again, stoichiometric amounts of reagents are desired, but an excess can be used.

A solvent is desirable. In general, polar and nonpolar, unreactive solvents can be used, including toluene, xylene, 1,4-dioxane, isopropanol, butanol, any of which can be either dry or moistened with water.

The times of reactions for the various reactions are not critical. Thus, any phase of the process can be carried out in from 1 to 8 hours.

The metal ion or metal ion-containing radical are selected such that the metal is one from Groups IIA, IIB, VIA and VIII of the Periodic Table (Fisher Scientific, 1978). Illustrative metals from the respective groups are calcium and strontium; zinc and cadmium; chromium and molybdenum; and nickel. These can be contained in salts having, for example, the carbonate, the halide (e.g. the chloride or bromide) or the nitrate ion. The metal may also be in the form of its oxide or hydroxide or it can be a portion of an acid, as, for example, molybdic acid. Generally preferred are the oxide, the carbonate and the halide.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, corrosion inhibitors, extreme pressure agents, viscosity index improvers, co-antioxidants, anti-wear agents and the like can be used. These materials do not detract from the value of the compositions of this invention, rather the materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characterisitcs. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions" Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the preformed adducts of the present invention may be employed in any amount which is effective for imparting the desired degree of friction reduction or antiwear activity. In many applications, however, the adduct is effectively employed in amounts from about 0.25% to about 10.% by weight, and preferably from about 1.0 to about 5.0% of the total weight of the composition.

The following Examples will present illustrations of the invention. They are illustrative only, and are not meant to limit the invention.

EXAMPLE 1

A one liter glass reactor fitted with a nitrogen inlet, stirrer, thermometer, Dean-Stark water trap and condenser was used for the reaction.

Oleic acid (1.0 mole, 282.0 grams), 2-amino-2-(hydroxymethyl)-1,3-propanediol (1.0 mole, 121.0 grams) and 200 m. of xylene were charged to the reactor.

The reaction mixture was heated, using a nitrogen purge and rapid stirring, to a maximum temperature of 162° C. and was maintained there for 13 hours. Water evolved over the temperature range of 125°–162° C. A total of 35 ml. of water (theory = 36 ml.) was collected. The product was di(hydroxymethyl) oleyl oxazoline.

Toluene (300 ml.) was added and $P_2S_5$ (0.55 mole, 122.1 grams) was added slowly over a period of two hours at a temperature of 70°–82° C. The reaction was run for a total of 12 hours over a temperature range of 70°–115° C. The reaction product was a clear, amber fluid. The toluene and xylene were removed by vacuum distillation. The product was a clear, amber, oil soluble solid at room temperature. A synthetic hydrocarbon diluent oil (502 grams) was added to give a product which was a clear, amber, low-melting, oil soluble gel.

EXAMPLE 2

The same reactor as described in Example 1 was used. The phosphosulfurized oxazoline of Example 1 (0.10 mole, 92.2 grams) and 400 ml. of toluene were charged to the reactor. 12.1 Grams of $Na_2MoO_4.2H_2O$ was dissolved in 100 ml. of water and acidified with sulfuric acid to a pH of 5.0–5.5. This molybdic acid solution was added to the reactor with rapid stirring at room temperature. The reaction mixture was heated with rapid stirring for a period of 3.5 hours over a temperature range of 21°–83° C.

The aqueous phase was separated and discarded. Toluene was removed from the product by vacuum distillation and the product was vacuum filtered through HiFlo filter aid. The product was a dark blue fluid.

EXAMPLE 3

The same reactor as described in Example 1 was used. The phosphosulfurized oxazoline of Example 1 (0.10 mole, 92.2 grams), zinc oxide (0.055 mole, 4.4 grams), 3 ml. of water and 400 ml. of toluene were charged to the reactor. The reactor mixture was heated with rapid stirring for 11 hours over a temperature range of 23°–95° C. The toluene and trace of water were removed by vacuum distillation. The product was vacuum filtered through HiFlo filter aid. The final product was a clear, pale yellow fluid.

EVALUATION OF THE COMPOUNDS

The compounds were evaluated in a low velocity friction apparatus (LVFA) in a fully formulated 5W-20 automotive engine oil. The compound was 4% (active ingredient) of the total weight of oil.

Description

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X–Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a low-cam-motor arrangement.

Procedure

The rubbing surfaces and 12–13 ml. of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 min. at 250° F., 240 psi, and 40 fpm sliding speed. Afterward, measurements of $U_k$ vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

| PERCENT REDUCTION IN COEFFICIENT OF FRICTION | | |
| --- | --- | --- |
| Compound | 5 ft./min. | 30 ft./min. |
| Base Oil Without Additive | 0% | 0% |
| Example 2 | 45% | 42% |
| Example 3 | 10% | 4% |

The compounds were also evaluated in the Shell 4-Ball Wear Test in a mineral oil stock containing 80% of a 150 second solvent paraffinic bright oil and 20% of a 200 second solvent paraffinic neutral oil.

In the test, three stationary balls are placed in a lubricant cup and a lubricant or a lubricant containing the compound to be tested is added thereto, and a fourth ball is placed in a chuck mounted on a device which can be used to spin the ball at known speeds and loads. The samples were tested using ½-inch stainless steel balls of 52100 steel, at a 60 Kg load for 30 minutes. Table 2 shows the results.

TABLE 2

4-BALL WEAR TEST

| Compound | Conc. Compound, Wt. %* | Temp., °F. | Wear Scar Diameter/mm | |
|---|---|---|---|---|
| | | | 1000 RPM | 2000 RPM |
| Base oil | — | Room | 0.90 | 3.10 |
| | | 200 | 2.00 | 2.70 |
| | | 390 | 2.40 | 2.90 |
| Example 2 | 2 | Room | 0.50 | 0.50 |
| | | 200 | 0.50 | 0.50 |
| | | 390 | 0.50 | 1.80 |
| Example 3 | 2 | Room | 0.50 | 2.00 |
| | | 200 | 0.60 | 2.00 |
| | | 390 | 1.00 | 1.10 |

*Active ingredient.

We claim:

1. A compound obtained by reaction of one equivalent of a carboxylic acid of the formula

R—COOH wherein R is a hydrocarbyl group containing 9 to 50 carbon atoms with tris(hydroxymethyl)aminomethane, reacting the resulting product with a phosphorus polysulfide and reacting the phosphorus-containing product with a metal-containing compound wherein the metal in said metal-containing compound is selected from Groups IIA, IIB, VIA or VIII of the Periodic Table.

7. The compound of claim 1 wherein the said acid is oleic, the said polysulfide is pentasulfide and the metal in said metal-containing compound is zinc.

8. A lubricant composition comprising a major proportion of a lubricant and a friction reducing or antiwear amount of a compound obtained by reaction of one equivalent of a carboxylic acid of the formula

R—COOH wherein R is a hydrocarbyl group containing 9 to 50 carbon atoms with tris(hydroxymethyl)aminomethane, reacting the resulting product with a phosphorus polysulfide and reacting the phosphorus-containing product with a metal-containing compound wherein the metal in said metal-containing compound is selected from Groups IIA, IIB, VIA or VIII of the Periodic Table.

9. The composition of claim 8 wherein the said acid is oleic.

10. The composition of claim 8 wherein the said polysulfide is pentasulfide.

11. The composition of claim 8 wherein the metal is molybdenum.

UNITED STATES PATENT AND TRADEMARK OFFICE
CERTIFICATE OF CORRECTION

PATENT NO. : 4,253,978
DATED : March 3, 1981
INVENTOR(S) : Robert M. Gemmill, Jr. and Andrew G. Horodysky It is certified that error appears in the above-identified patent and that said Letters Patent are hereby corrected as shown below:

Column 3, line 19, "The final reaction...." should start a new paragraph.

Column 4, line 49, "characterisitcs" should read --characteristics--.

Column 5, line 13, "m." should read --ml.--.

Column 6, line 13, "Y" should be --$\underline{Y}$-- and "X-Y" should be --$\underline{X}$-$\underline{Y}$--.

Signed and Sealed this

Sixteenth Day of June 1981

[SEAL]

Attest:

RENE D. TEGTMEYER

Attesting Officer    Acting Commissioner of Patents and Trademarks